United States Patent [19]
Jacobs et al.

[11] Patent Number: 5,304,292
[45] Date of Patent: Apr. 19, 1994

[54] ELECTROPHORESIS GELS

[75] Inventors: Michael Jacobs, East Norwalk; George T. Leka, Trumbull, both of Conn.

[73] Assignee: Jule, Inc., New Haven, Conn.

[21] Appl. No.: 968,296

[22] Filed: Oct. 29, 1992

[51] Int. Cl.[5] .............................................. C25B 9/00
[52] U.S. Cl. ................................ 204/299 R; 204/182.8
[58] Field of Search ........................ 204/299 R, 182.8

[56] References Cited
U.S. PATENT DOCUMENTS
4,909,918 3/1990 Bambeck et al. ................ 204/182.8

Primary Examiner—T. Tung
Assistant Examiner—C. Delacroix-Muirheid
Attorney, Agent, or Firm—John R. Doherty

[57] ABSTRACT

An electrophoresis device comprising a pair of electrically-insulating, liquid impermeable sheets disposed in spaced apart relationship to one another and a gel membrane disposed between the sheets acting as an electrophoresis medium, the gel membrane having a substantially flat surface thereon disposed below an edge of the sheets defining together with the sheets an elongated slot of predetermined thickness, wherein at least one liquid impermeable, elastomeric, compliant member, such as a solid cylinder or tube, is disposed within the slot and forms at least one sample well above the gel membrane.

13 Claims, 4 Drawing Sheets

ELECTROPHORESIS GELS

BACKGROUND OF THE INVENTION

This invention relates to an improved electrophoresis device.

Electrophoresis gels are widely used for separating and analyzing biomolecular materials such as proteins and nucleic acids, for example. A gel medium, such as polyacrylamide, agarose or combinations thereof, is commonly disposed between a pair of electrically-insulating, liquid impermeable sheets such as glass or plastic plates which are held in spaced-apart, opposing relationship by insulating spacers or the like. During use, sample liquids, which are to be subjected to electrophoresis, are placed, layered or injected into sample wells at the top of the gel medium and electrophoresis is begun by applying electrical power to the gel medium.

In the prior art, sample wells have been formed by inserting a comb shaped plastic member into the gel solution while it is still a liquid. After polymerization has occurred, the comb is removed and the sample wells are formed in the location where the teeth of the comb resided in the gel. The formation of consistently good sample wells in gels where the concentration of acrylamide is low has been generally unreliable and inconsistent using this technique. Low concentrations of acrylamide or other media provides a wider spectrum of biomolecules to be separated, particularly large size biomolecules.

Another technique that has been used to form sample wells is to first pour a gel with a flat top surface. A plastic insert is then placed on top of the surface to form the wells. The plastic insert, however, has not proven reliable in sealing the wells against leakage. Sample liquid leaks past some of the wells and contaminates adjoining wells.

The prior art techniques generally rely upon the fits and clearances between the plastic comb or insert and the slot or opening provided between the glass plates in order to accommodate them. The slot or opening between the glass or plastic plates is generally created by spacers which are typically made from plastic sheet material. The slot openings or gel thickness tolerances between the combs and spacers can vary significantly enough to negatively affect the formation of the sample wells using prior art techniques for forming sample wells.

It will be apparent that the prior art has thus far failed to provide a reliable, economical solution to forming consistent sample wells particularly in large size gels and gel media of low concentration or poor characteristics. Instead, manufacturers of precast (ready made) gels have resorted to producing gels with flat tops, thus leaving to the individual researcher the task of forming the sample wells on top of the resolving gels. The researcher will ordinarily utilize either one of the above described techniques for forming the wells.

It is therefore an important object of the invention to provide an improved electrophoresis device employing a gel medium together with preformed sample wells wherein the sample wells are of consistently good quality. Another object of the invention is to provide such an improved electrophoresis device which eliminates high rejection rates of precast gels due to faulty wells in order to economically justify the production of precast or ready made gels on a large scale commercial basis.

SUMMARY OF THE INVENTION

The present invention provides an improved electrophoresis device comprising a gel medium disposed between a pair of electrically-insulating, liquid impermeable sheets, such as glass or plastic plates, which are held in opposing relationship to one another by a separating means or spacer member. The gel medium is formed with a substantially flat surface below an edge of at least one of the sheets defining together with the sheets an elongated cavity of predetermined thickness which communicates with the gel medium. At least one liquid impermeable, compliant, elastomeric member is disposed within the cavity and forms together with the sheets and the flat surface on the gel medium at least one sample well above the gel medium. The compliant, elastomeric member has a dimension which is at least slightly greater than the thickness of the elongated cavity such that the elastomeric member is at least slightly compressed between the sheets. The elastomeric member also has an end portion which is at least slightly compressed against the flat surface formed on the gel medium and/or slightly embedded into the gel medium, thereby substantially immobilizing the elastomeric member within the cavity and providing a liquid-tight seal so as to form at least one or a plurality of sample well.

The elastomeric, compliant, sample well-forming members generally may be of almost any shape or configuration but preferably are cylindrical or tubular having a diameter which is at least slightly greater than the thickness of the gel medium between the pair of electrically insulating sheets. Solid cylinders or hollow tubes of an elastomeric material, such as rubber or silicone, are highly desirable for use as the sample well-forming members in the practice of the invention. Soft or low durametric, hollow, rubber or silicone tubes are most preferred because they are more highly compliant and when inserted inside the elongated cavity, they are more easily compressed against the glass plates and the flat surface of the gel medium to form a tight and reliable seal.

The elastomeric cylinders or tubes may be disposed at spaced apart intervals along the length of the elongated cavity to provide between them a multiplicity of sample wells which communicate directly with the gel medium for carrying out the electrophoresis process. The cylinders or tubes are easily inserted between the glass plates and can be placed to provide sample wells of equal or varying size or volumes. The cylinders or tubes may also be connected to a common holder to form a comb shaped insert which can remain in place during electrophoresis or which can be removed after the cylinders or tubes have been positioned properly inside the device. The use of hollow tubes having partially closed ends are particularly advantageous since they provide a means for easily compressing the tube ends against the flat surface of the gel medium using a rod or similar tool placed inside the tube.

Hollow tubes, which are open at both ends, can also be employed to form the sample wells using the interior or inside diameter volume of the tubes instead of the spaced intervals between them, that is, sample can be inserted into the hollow tubes for electrophoresis.

The elastomeric cylinders or tubes are compressible and therefore conform to variations in the slot or cavity formed between the glass plates much better than the plastic materials used in the prior art. The soft cylinders or tubes provide an ideal hydraulic seal to create the sample wells which prevents them from leaking and contaminating adjacent wells. The novel principles of the invention are not limited to producing only large electrophoresis gels but can also be employed to produce small or mini gels as well.

BRIEF DESCRIPTION OF THE DRAWING

The invention will now be described in greater detail with particular reference to the accompanying drawings which show several preferred embodiments thereof and wherein.

DESCRIPTION OF THE PREFERRED EMBODIMENTS

Figure 1:
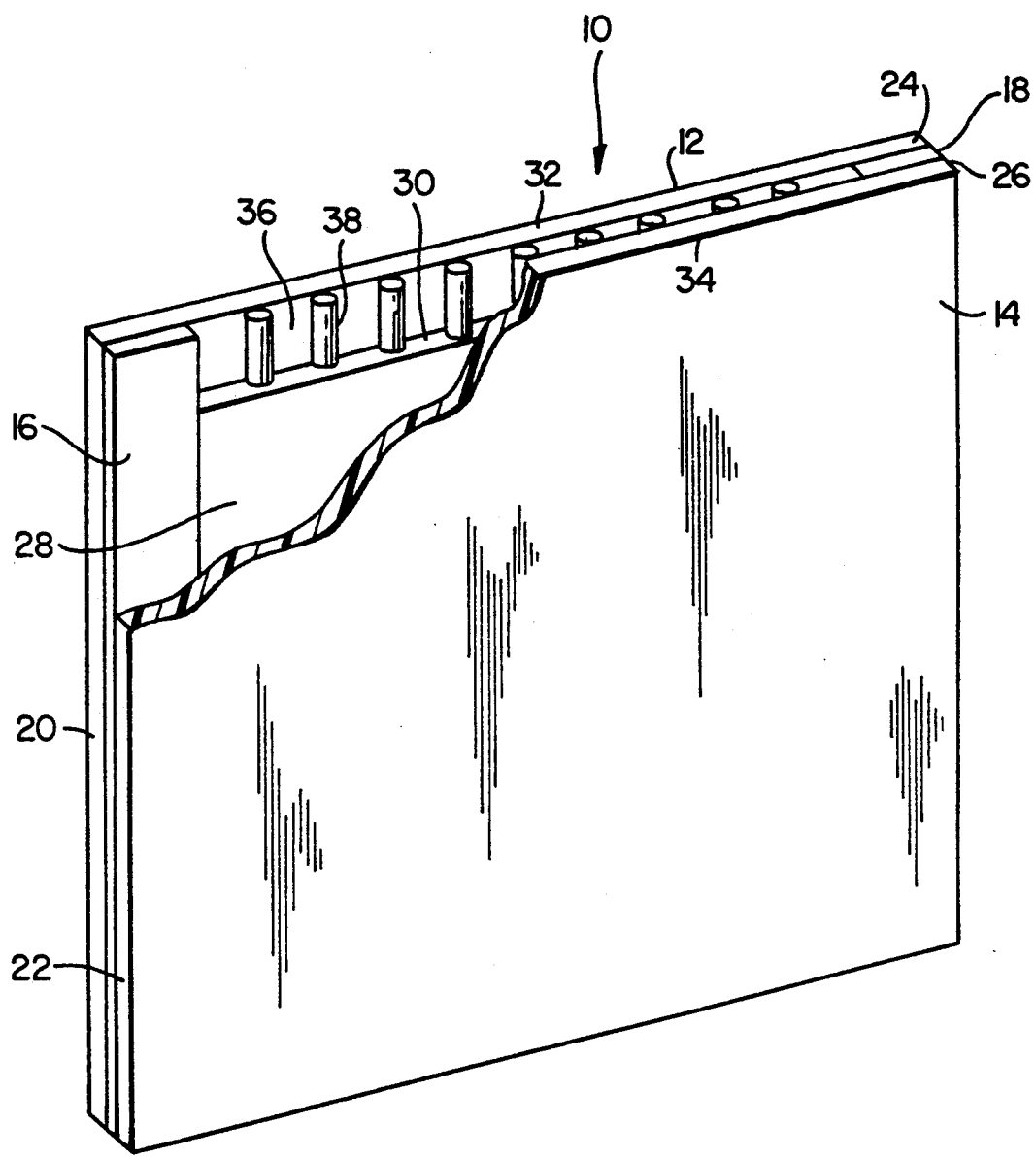
FIG. 1 is a perspective, partially cut away view of an electrophoresis device embodying the principles of the invention.
Figure 2:
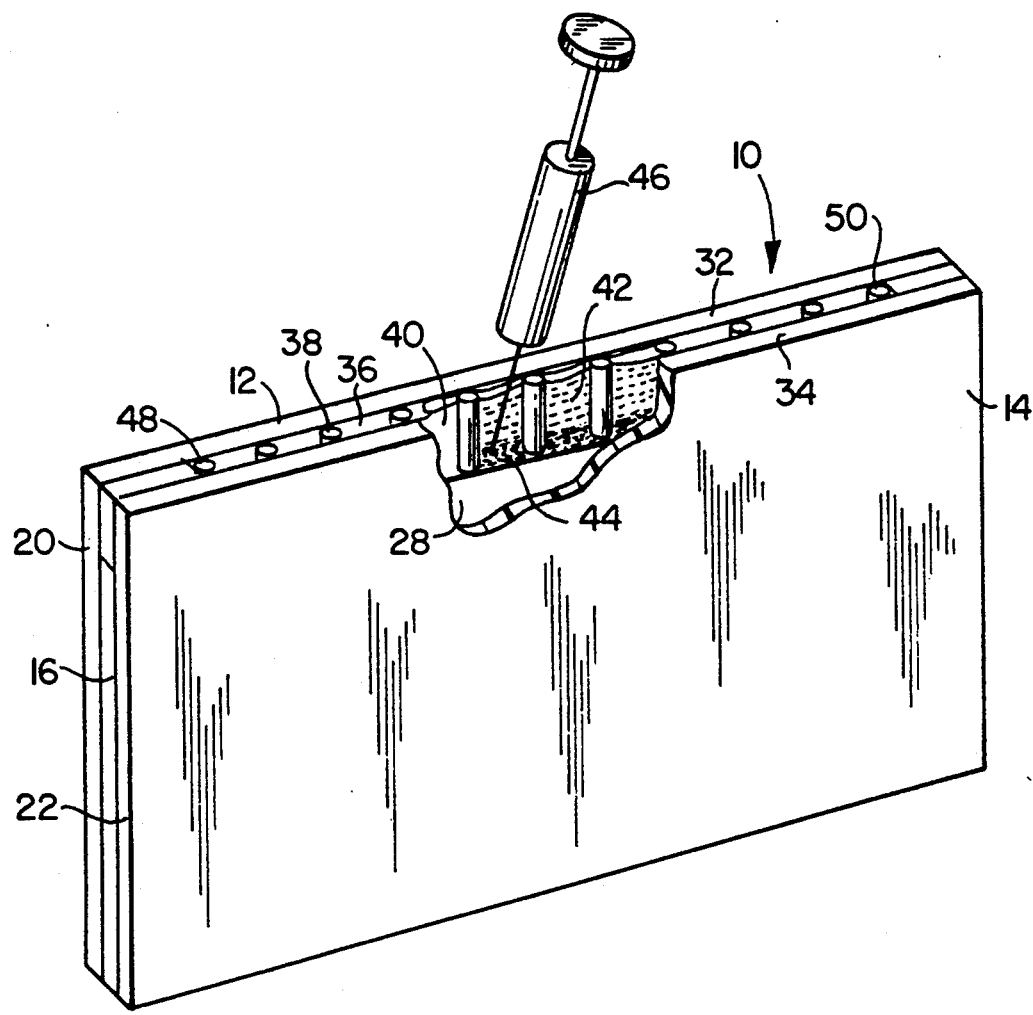
FIG. 2 is a similar view showing some of the sample wells in the electrophoresis device being filled with a liquid sample solution using a syringe.

Referring now to the drawing and particular to FIGS. 1 and 2, there is shown an electrophoresis device 10 according to a preferred embodiment of the invention. The device includes a pair of rectangular, electrically insulating, liquid impermeable sheets 12, 14 such as glass or plastic plates, for example, which are separated in opposing relationship to one another by a pair of spacer members 16, 18. The spacer members 16, 18 are positioned between the two sheets 12, 14 along the opposite lateral or vertical edges of the sheets as shown at 20, 22 and 24, 26, respectively, and may be secured directly to the sheets such as by gluing or in any other conventional manner. A gel membrane or slab 28 is formed between the opposing sheets 12, 14 by pouring a liquid gel solution, such as polyacrylamide, into the space between the sheets and allowing sufficient time for the gel to set up or polymerize to form the gel membrane or slab. The gel membrane will have a thickness of between about 0.0001 mm. and 3.0 mm. for small and large size gels. The size of the sheets or plates will vary depending upon the particular application.

The gel membrane or slab 28 is formed at the top of the electrophoresis device 10 with a substantially flat surface 30 according to the principles of the invention. The flat surface 30 is disposed a predetermined distance, for example, below top edges 32, 34 of the two sheets 12, 14, respectively, leaving an elongated slot 36 at the top of the device. The slot 36 is bordered on each side by one of the two spacer members 16, 18 and communicates directly with the gel membrane 28.

A multiplicity of individual, elastomeric sample well-forming members 38 in the form of solid cylinders or hollow tubes, for example, are disposed in spaced apart relation to one another within the slot 36, there being nine such cylinders or tubes shown in the embodiment of FIG. 1 for purposes of illustration only. The cylinders or tubes 38 are made from a soft, elastomeric material such as rubber or silicone, for example. The cylinders or tubes should be made of an elastomeric material which is relatively soft and compliant and which preferably has a short durometer value ranging from between about 40 and 70. A silicone tube having a durometer value of 50 has been used successfully for this purpose.

It is important in the practice of the invention that the sample well-forming members 38 have a dimension or diameter, in the case of the cylinders or tubes, which is at least slightly greater than the thickness of the slot 36. This assures that the sample well-forming members will be compressed against the side walls of the sheets 12, 14 when inserted into the slot 36, thereby forming a tight hydraulic seal at their interfaces. The tight interference fit substantially immobilizes the members within the slot 36, however, the fit should not be so tight as to prevent movement of the members to adjust their position after insertion. Also, the size of the cylinders or tubes should not be so great as to force the pair of sheets or glass plates apart and thus destroy the integrity of the electrophoresis device.

It is also important in the practice of the invention that the sample well-forming members 38 should be at least slightly compressed against the flat surface 30 on top of the gel membrane 28. The degree of compression should be sufficient to assure a good liquid tight seal between the end of each member and the gel membrane 28. It is also desirable, but not necessary, that each sample well-forming member 38 should be long enough to extend the full depth of the slot 36 and thus maximize the size of each sample well. This also enhances the insertion and placement of the members inside the slot 36 and additionally the compression of the members against the flat surface 30.

As shown more particularly in FIG. 2, the cylinders or tubes 38 are positioned vertically inside the slot 36 and divide the slot into separate or individual sample wells 40, there being ten such wells shown in this embodiment, which are then filled with buffer solution as shown at 42. A liquid sample 44 containing a biomolecular material, e.g. protein, is then deposited at the bottom of the well 40 using a syringe 46, for example. Since the soft elastomeric cylinders or tubes 38 effectively seal off each individual sample well 40, there is no opportunity for the sample to migrate into adjacent wells and contaminate adjacent samples therein.

It will also be noted in the electrophoresis device shown in FIG. 2 that soft elastomeric cylinders 48, 50 are inserted at each end of the elongated slot 36 adjacent to the spacer members 16, 18, respectively. These cylinders assure that no leakage occurs of the upper buffer down along side the spacer and into the lower buffer tank region. This prevents electrical current leakage which can otherwise cause the sample undergoing electrophoresis in the outer lanes of the gel to run skewed.

Figure 3:
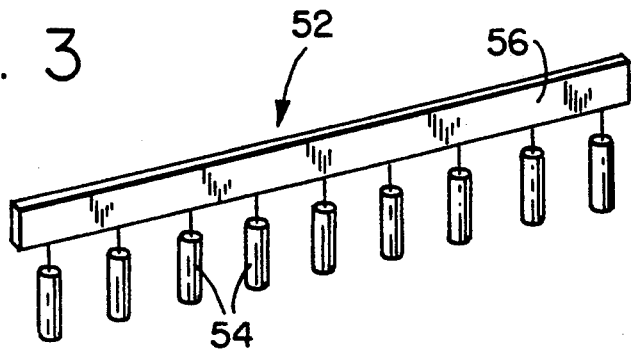
FIG. 3 is a perspective view of a plurality of elastomeric sample well-forming cylinders attached to an elongated holder forming a comb-like insertion member.

FIG. 3 shows a comb-like assembly 52 wherein a plurality of sample well-forming members 54 are attached to an elongated holder or bar 56. The members 54 which may be solid cylinders, for example, are inserted together at one time inside the slot 36. The cylinders can remain in the slot during the sample loading and running process, and then later removed and reused in other gels. The holder or bar 56 can also be pulled away from the individual cylinders leaving the sample well-forming members 54 inserted in the gel slot. This insertion device provides an effective method for inserting multiple cylinders during the manufacture of the electrophoresis device.

Figure 4:
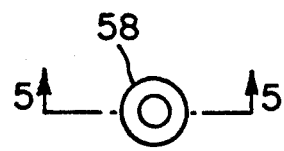
FIG. 4 is a top plan view of a hollow elastomeric tube useful in the practice of the invention.
Figure 5:
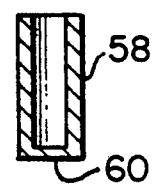
FIG. 5 is an elevational, sectional view taken along the line 5—5 in FIG. 4.

In FIGS. 4 and 5, there is shown an elastomeric tube 58 having a closed end 60. This tube structure is ideal for use as the sample well-forming member since it greatly facilitates attainment of the leakproof seal at the flat surface 30 of the gel. A rod or similar instrument can be inserted inside the tube 58 and pushed downwardly until the closed end 60 contacts the surface 30.

Figure 6:
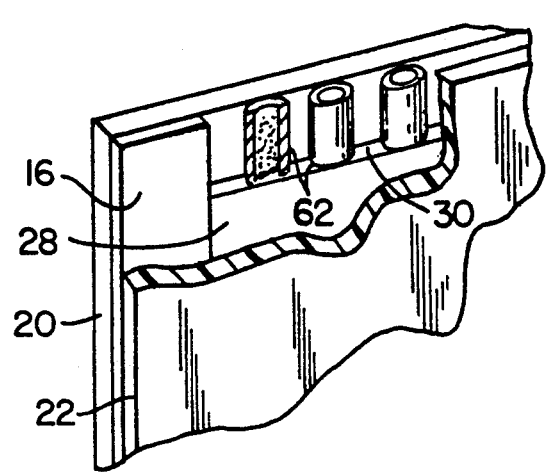
FIG. 6 is a fragmentary, perspective, partially cut away view of an electrophoresis device incorporating another embodiment of the invention.

Another embodiment of the invention is shown in FIG. 6 wherein the interior section of hollow elastomeric tubes 62 form the sample wells on top of the flat surface 30. Here again it is important to achieve a good leakproof seal between the tube ends and the surface of the gel.

Figure 7:
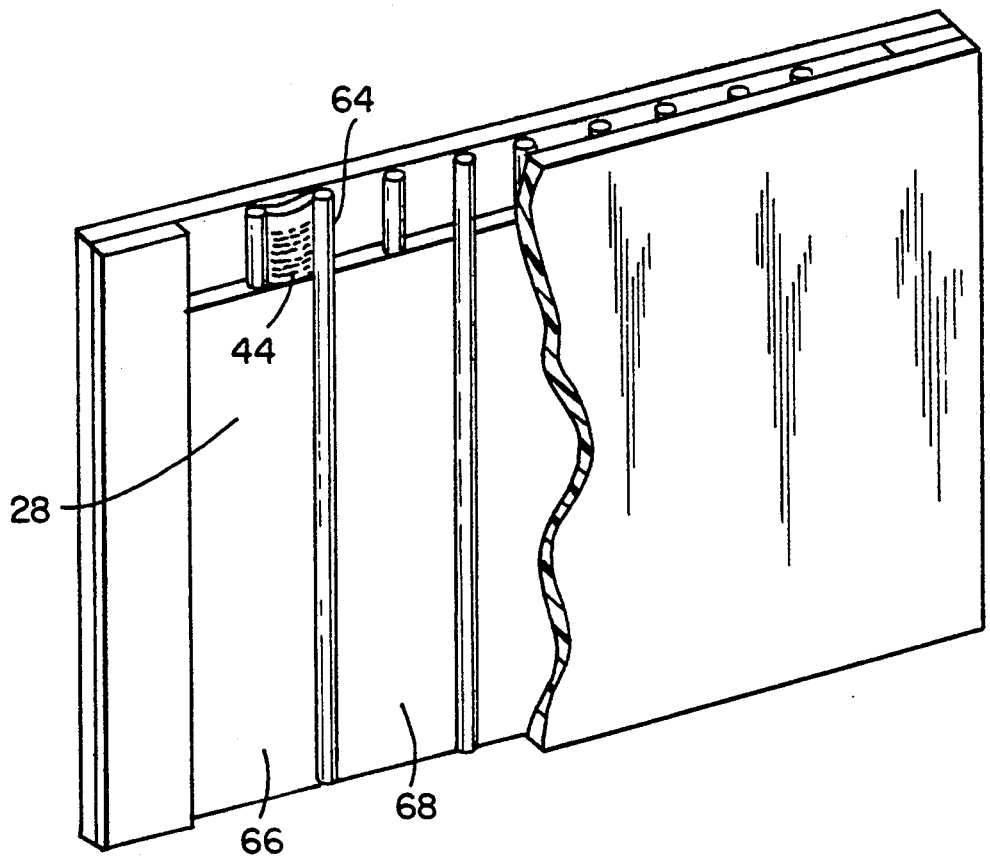
FIG. 7 is a similar view showing another embodiment.

FIG. 7 shows still another embodiment wherein elastomeric cylinders 64 are used to partition a gel membrane or slab. The cylinders or tubing are positioned to extend the length of the gel in order to divide the slab into separate sections 66, 68. A different concentration of acrylamide can then be placed in each section. The separate sections can also be used for segregation of different sample materials.

Figure 8:
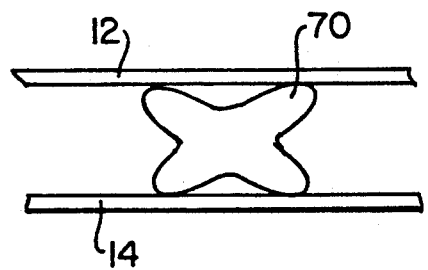
FIG. 8 is a similar view of a wing shaped sample well-forming member.
Figure 9:
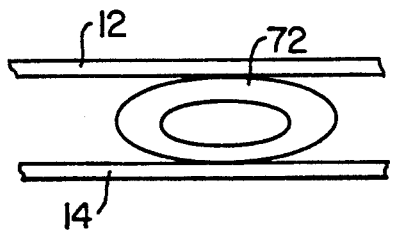
FIG. 9 is a view similar to FIG. 4 showing a hollow elastomeric tube having an elliptical cross-section which can also be used in the practice of the invention.

Although the sample well-forming members are preferable cylinders or tubes as described above, it is entirely possible of course to employ other shapes and configurations such as the wing-shaped insert 70 shown in FIG. 8 or the elliptical tube 72 shown in FIG. 9. The important factor in choosing the sample well-forming member is that the member must be elastomeric and compliant as distinguished from the plastic comb-like devices of the prior art. It will also be understood that while the invention has been described herein with particular reference to vertical electrophoresis devices, the invention is applicable to horizontal electrophoresis devices as well.

What is claimed is:

1. An electrophoresis device, comprising, in combination:
    a pair of electrically-insulating, liquid impermeable sheets disposed in opposing relationship to one another;
    means for separating said sheets a predetermined distance from one another;
    a gel membrane disposed between said sheets acting as an electrophoresis medium, said gel membrane having a substantially flat surface thereon disposed a distance from an edge of said sheets defining together with said sheets an elongated slot of predetermined thickness communicating with said gel membrane; and
    at least one liquid impermeable, elastomeric, compliant cylinder disposed within said slot in contact with said sheets and said flat surface of said gel membrane forming at least one sample well bound by said cylinder, said flat surface of said gel membrane and both of said sheets, said cylinder being at least slightly compressed between said sheets and against said flat surface of said gel membrane, thereby substantially immobilizing said cylinder within said slot and providing a liquid-tight seal around said sample well.

2. An electrophoresis device according to claim 1, wherein said elastomeric, compliant cylinder is a solid cylinder.

3. An electrophoresis device according to claim 1, wherein said elastomeric, compliant member is a hollow tube.

4. An electrophoresis device according to claim 3, wherein said hollow tube has a closed end which contacts said flat surface of said gel membrane.

5. An electrophoresis device according to claim 3, wherein the interior volume of said hollow tube forms said sample well.

6. An electrophoresis device according to claim 1, wherein a multiplicity of said elastomeric, compliant cylinders are disposed within said slot.

7. An electrophoresis device according to claim 6, wherein at least one of said elastomeric, compliant cylinders penetrates through said gel membrane and partitions said membrane into separate sections.

8. An electrophoresis device according to claim 1, wherein said elastomeric, compliant cylinder is composed of rubber or silicone material.

9. An electrophoresis device according to claim 1, wherein said electrically insulating, liquid impermeable sheets are composed of glass or plastic sheets.

10. An electrophoresis device according to claim 1, wherein said means for separating said sheets comprises a pair of electrically non-conductive strips one of each of which is disposed between said sheets along an opposite edge thereof.

11. An electrophoresis device according to claim 10, wherein an elastomeric, compliant cylinder is disposed adjacent to each one of said strips within said slot.

12. A method of forming a sample well in an electrophoresis device including a pair of electrically-insulating, liquid impermeable sheets disposed in opposing relationship to one another and a gel membrane disposed between said sheets and having a substantially flat surface thereon disposed below an edge of said sheets defining together with said sheets an elongated slot of predetermined thickness, comprising
    providing at least one liquid impermeable, elastomeric, compliant cylinder having a diameter which is at least slightly greater than the thickness of said slot; and
    inserting said cylinder within said slot in contact with said sheets and said flat surface of said gel membrane forming a sample well bound by said cylinder and both of said sheets, said cylinder being at least slightly compressed between said sheets and against said flat surface, thereby substantially immobilizing said cylinder within said slot and providing a liquid-tight seal around said sample well.

13. An electrophoresis device, comprising, in combination:
    a pair of electrically-insulating, liquid impermeable sheets disposed in opposing relationship to one another;
    means for separating said sheets a predetermined distance from one another;
    a gel membrane disposed between said sheets acting as an electrophoresis medium, said gel membrane having a substantially flat surface thereon disposed a distance from an edge of said sheets defining together with said sheets an elongated slot of predetermined thickness communicating with said gel membrane; and at least two separate, liquid impermeable, elastomeric, compliant, cylinders disposed in spaced apart relation within said slot, said cylinders contacting both of said sheets and said flat surface of said gel membrane forming a sample well between said cylinders and adjacent to said flat surface, said cylinders being at least slightly compressed between said sheets and against said flat surface of said gel membrane, thereby substantially immobilizing said cylinders within said slot and providing a liquid-tight seal around said sample well.

* * * * *